(12) United States Patent
Schwager et al.

(10) Patent No.: US 9,138,565 B2
(45) Date of Patent: Sep. 22, 2015

(54) GUIDE WIRE

(75) Inventors: Michael Schwager, Winterthur (CH); Karl Konstantin Haase, Reutlingen (DE)

(73) Assignee: SCHWAGER MEDICA AG, Winterthur (CH)

( * ) Notice: Subject to any disclaimer, the term of this patent is extended or adjusted under 35 U.S.C. 154(b) by 659 days.

(21) Appl. No.: 13/499,213

(22) PCT Filed: Sep. 29, 2010

(86) PCT No.: PCT/CH2010/000234
§ 371 (c)(1),
(2), (4) Date: Jun. 11, 2012

(87) PCT Pub. No.: WO2011/038522
PCT Pub. Date: Apr. 7, 2011

(65) Prior Publication Data
US 2012/0238872 A1    Sep. 20, 2012

(30) Foreign Application Priority Data
Sep. 30, 2009   (CH) .................................... 1506/09

(51) Int. Cl.
*A61M 25/09* (2006.01)

(52) U.S. Cl.
CPC .......... *A61M 25/09* (2013.01); *A61M 25/09016* (2013.01); *A61M 25/09033* (2013.01); *A61M 2025/091* (2013.01); *A61M 2025/09083* (2013.01); *A61M 2025/09175* (2013.01)

(58) Field of Classification Search
CPC ................. A61M 25/09016; A61M 25/09033; A61M 25/09; A61M 2025/091; A61M 2025/09083; A61M 2025/09175
USPC ........... 604/27, 506–508, 510, 524–525, 528; 600/434, 585
See application file for complete search history.

(56) References Cited

U.S. PATENT DOCUMENTS 4,964,409 A    10/1990   Tremulis
5,050,606 A *  9/1991   Tremulis ....................... 600/486
(Continued)

FOREIGN PATENT DOCUMENTS

EP    0313836 A2    5/1989
EP    0343509 A2    11/1989
(Continued)

OTHER PUBLICATIONS

Japanese Office Action dated Aug. 4, 2014 in English.

*Primary Examiner* — Theodore Stigell
*Assistant Examiner* — Amber Stiles
(74) *Attorney, Agent, or Firm* — Birch, Stewart, Kolasch & Birch, LLP (57) ABSTRACT

A guide wire for a catheter comprises an elongated hollow shaft has a lumen for delivering or leading away the fluid, and an insertion aid in the form of a flexible wire coil connected coaxially to a distal end of the hollow shaft. The wire coil has a guide wire tip arranged at a distal end, a core wire being arranged in the lumen of the hollow shaft to control the flexibility of the guide wire. The core wire extends out of the lumen and through the wire coil to the guide wire tip. A distal inner area of the wire coil adjacent to the guide wire tip in a proximal direction communicates with the lumen of the hollow shaft by means of a fluid channel formed next to the core wire and has at least one outwardly open passage opening for the fluid to be introduced or removed.

25 Claims, 3 Drawing Sheets

(56) References Cited

U.S. PATENT DOCUMENTS

| | | | | |
|---|---|---|---|---|
| 5,211,636 A | * | 5/1993 | Mische | .................. 604/264 |
| 5,322,508 A | | 6/1994 | Viera | |
| 7,025,758 B2 | * | 4/2006 | Klint | .................. 604/524 |
| 2007/0213689 A1 | | 9/2007 | Grewe et al. | |

FOREIGN PATENT DOCUMENTS

| | | |
|---|---|---|
| EP | 0397 173 A1 | 5/1990 |
| EP | 0806220 A2 | 11/1997 |
| JP | 3-90166 A | 4/1991 |
| JP | 2000-501010 A | 2/2000 |
| JP | 2002-233574 A | 8/2002 |
| WO | WO 93/04722 A2 | 3/1993 |
| WO | WO 96/13295 A1 | 5/1996 |
| WO | WO 97/11735 A1 | 4/1997 |
| WO | WO 97/19713 A2 | 6/1997 |
| WO | WO 97/32518 A1 | 9/1997 |
| WO | WO 97/49447 A1 | 12/1997 |

* cited by examiner

GUIDE WIRE

TECHNICAL FIELD

The invention relates to a guide wire for a catheter, designed to introduce and/or remove fluids in human and/or animal hollow organs, in particular in blood vessels, comprising an elongate hollow shaft with a lumen for delivering and/or withdrawing the fluid, and an insertion aid in the form of a flexible wire coil attached coaxially to a distal end of the hollow shaft, with a guide-wire tip arranged at a distal end, a core wire being arranged in the lumen of the hollow shaft in order to control a flexibility of the guide wire, which core wire extends out of the lumen in a longitudinal direction and right through the wire coil to the guide-wire tip. The invention further relates to a method for the diagnostic and/or therapeutic treatment of vessels and/or tumors and to a use of a guide wire for diagnostic and/or therapeutic purposes on the human and/or animal body.

PRIOR ART

Guide wires usually serve as aids for inserting catheters into human and/or animal hollow organs. The guide wires are pushed into the hollow organ before the insertion of the catheter and are positioned at a desired location. To do this, the guide wires have to be sufficiently flexible and thin at the distal end, for example in order also to follow narrow and strongly curved vessel profiles. At the same time, however, the guide wires must also have sufficient stiffness to ensure that they can be pushed forward from the direction of the proximal end.

Hollow guide wires are also known which, for example, are used to introduce and/or remove liquid and act as pressure measurement probes in a hollow organ. In the proximal part, guide wires of this kind have, for example, a hollow steel tube which, at the distal end, has a relatively flexible helical spring with a guide-wire tip. In order to control the stiffness of the guide wire, a core wire, for example, is mounted on the distal end of the steel tube, which core wire extends through the helical spring as far as the guide-wire tip. In the area of the proximal end of the helical spring, the core wire is also welded to the latter all the way round, in order to permit a defined sliding of the guide wire.

In order to deliver and/or withdraw a fluid through the guide wire, one or more lateral openings are formed in the steel tube behind the wire coil. In this way, a fluid can be delivered through the hollow guide wire and the lateral openings into the hollow organ, or a fluid is removed from the hollow organ through the lateral openings and the guide wire. A hollow guide wire, which is used as a pressure measurement probe, is described, for example, in WO 97/32518 (Scimed Life Systems Inc.).

A deflectable guide wire for infusions is known from US 2007 213 689 A1 (Johnson & Johnson). The steerable end is formed by a wire coil. To be able to direct the infusion liquid into the area of the wire coil, the guide wire accommodates an independent infusion tube, which extends from the proximal end into the area of the wire coil, where the therapeutic liquid can flow out of the guide wire through the gaps between the windings of the wire coil. The wire coil is accommodated between an inner and an outer jacket made of plastic. A disadvantage here is that a separate infusion tube has to be accommodated in the guide wire and that the release of the liquid in the coil area cannot be controlled.

WO 97/11735 A1 (Interventional Innovations) discloses a guide wire whose distal part has a smaller diameter than the proximal part. An open wire coil made of tungsten or platinum is secured on the distal part of the guide wire, in order to make the distal tip of the guide wire softer for protecting tissue. A rod element protruding from a distal end of the hollow wire and into the wire coil is provided with a groove for the liquid exchange. The open wire coil is not suitable for the transport of liquid, such that the liquid can only be released exactly where the groove emerges from the guide wire.

U.S. Pat. No. 5,322,508 A (Cordis Corporation) discloses another guide wire having a transport system for liquid. A wire coil is wound onto a core wire, and a plastic jacket is applied to the outside of the wire coil. The liquid is advanced in a helical line configuration in the interstices of the coil. The liquid can emerge at the end of the plastic enclosure. A disadvantage is that guiding the liquid in a helical line configuration results in a very long and narrow channel with correspondingly high flow resistance.

U.S. Pat. No. 5,211,636 A (Lake Region Manufacturing) proposes a guide wire composed of an outer and an inner helical spring, in the center of which a core wire is arranged. The outer helical spring has the structure of a ribbon shaped as a helical line and made up of four coil wires extending parallel to one another and connected to one another. The inner helical spring is formed by a single wire, with a spacing present between adjacent windings. The coils are routed in opposite directions, such that the guide wire is able to transmit a torque. The main part of the helical spring is wound tightly in order to achieve maximum control of the guide wire. The helical wire is wound with spacings at the distal end, and the spacings between the windings serve as infusion openings. A membrane is provided on the inner face of the inner coil or between inner coil and outer coil, such that the central lumen, in which the core wire is also located, can be used as a channel for the infusion liquid.

However, the currently known hollow guide wires for delivering and/or withdrawing a fluid are not completely satisfactory.

There is therefore still a need for an improved and easily insertable guide wire for delivering and/or withdrawing a fluid.

DISCLOSURE OF THE INVENTION

The object of the invention is to make available an easily insertable guide wire which belongs to the technical field mentioned at the outset and which permits more precise introduction and/or removal of fluids in human and/or animal hollow organs.

The object is achieved by the features defined in claim 1. According to the invention, a distal inner area of the wire coil, adjacent to the guide-wire tip in a proximal direction, communicates with the lumen of the hollow shaft via a fluid channel formed alongside the core wire and also has at least one outwardly open through-opening for the fluid that is to be introduced and/or removed.

In this context, a wire coil is to be understood in particular as a hollow cylindrical structure which is formed by a wire wound helically about a longitudinal axis. The wire coil is formed in particular from a metal wire, e.g. of platinum. However, the wire of the wire coil does not necessarily have to be made of metal. It is also conceivable in principle to provide a wire made of plastic.

The core wire is made in particular from metal, for example from steel. In principle, however, other materials can also be used for the core wire, e.g. high-strength plastics and/or composite materials.

By means of the through-opening being arranged according to the invention in a distal inner area of the wire coil adjacent to the guide-wire tip, the through-opening lies in an area in direct proximity to the guide-wire tip. In combination with the fluid channel between the distal inner area and the lumen of the hollow shaft, a fluid can thus be introduced from the guide wire into a hollow organ directly in an area of the guide-wire tip and/or removed therefrom. The at least one opening of the distal inner area of the wire coil is preferably directly adjacent, in the proximal direction, to the guide-wire tip.

Since the position of the guide-wire tip in a hollow organ can generally be determined relatively precisely, e.g. by known imaging methods, for example using X-rays, the proximity of the at least one through-opening to the guide-wire tip also means that the position of the at least one through-opening can be determined very exactly. Particularly in comparison with known guide wires in which the through-openings are arranged in the proximal direction behind the wire coil, the position of the through-opening in the guide wire according to the invention can therefore be determined more precisely.

Because of the core wire extending from the lumen through the wire coil as far as the guide-wire tip, the elasticity of the guide wire in its distal areas can also be adjusted very exactly, which additionally improves the insertability and controllability of the guide wire in a hollow organ. It is specifically possible, for example, for abrupt changes of elasticity in the area of the transition between hollow shaft and wire coil to be compensated by the core wire, which, for example, counteracts a kinking of the guide wire during insertion. Likewise, the elasticity of the usually superelastic wire coil can be reduced by the core wire and adapted to the specific requirements. It is thus possible, in particular, to use wire coils with especially small wire diameters, which in particular saves space. The guide wire or the guide-wire tip can thus be moved or maneuvered in a more targeted and more precise manner to a desired location in the hollow organ. As has been shown, in combination with the inventive arrangement of the through-opening, it is thus possible to increase to a surprising extent the precision with which fluids are introduced and/or removed in human and/or animal hollow organs.

Moreover, the solution according to the invention permits a space-saving and compact construction, since the fluid channel between the lumen and the distal inner area of the wire coil can extend entirely within the lumen and the wire coil. A free space is preferably formed alongside the core wire in the lumen of the hollow shaft and/or in the inner area of the wire coil, said free space functioning as a fluid channel. In a particularly advantageous embodiment, the hollow shaft has, at its distal end, a front opening which communicates with a front opening at the proximal end of the wire coil. The cross-sectional surface areas of the two front openings on the hollow shaft and on the wire coil are advantageously larger than a cross-sectional surface area of the core wire in this area. In this way, a free space permitting passage of the fluid remains alongside the core wire.

In a construction of this kind, the guide wires according to the invention can be designed with a cross-sectional surface area that is substantially constant along their entire length or that decreases continuously toward the guide-wire tip, which in turn improves the insertability of the guide wire.

The distal end of the hollow shaft and the proximal end of the wire coil are, for example, welded and/or adhesively bonded to each other. In particular, a proximal end of the wire coil can bear with its face on a distal end of the hollow shaft. However, it is also possible to push the proximal end of the wire coil onto the distal end of the hollow shaft, such that the proximal end of the wire coil surrounds the distal end of the hollow shaft. An arrangement in which the proximal end of the wire coil is pushed into the distal end of the hollow shaft is also advantageous. In this case, the distal end of the hollow shaft surrounds the proximal end of the wire coil.

Overall, the guide wires according to the invention are easily insertable into human and/or animal hollow organs and also permit highly precise and targeted introduction and/or removal of fluids at defined locations in human and/or animal hollow organs.

Preferably, a fluid-permeable connection between wire coil and core wire is present in an area of a proximal end of the wire coil, such that the wire coil is mechanically fixed relative to the core wire, and the distal inner area of the wire coil communicates with a proximal inner area of the wire coil lying proximally from the fluid-permeable connection. In this way, in particular, a still more precise sliding of the guide wire in a hollow organ is possible, since compressions and/or expansions of the wire coil in the longitudinal direction are almost completely prevented, without thereby substantially impairing the transverse flexibility of the guide wire. Since the connection between wire coil and core wire is in particular fluid-permeable, the proximal inner area lying proximally from the connection still nevertheless communicates with the distal inner area of the wire coil lying distally from the connection. In this way, even with a stable mechanical connection between core wire and wire coil, it is possible to easily obtain a fluid channel extending in the longitudinal direction through the wire coil.

If necessary, e.g. in the case of very long wire coils, it is possible for several fluid-permeable connections to be arranged, spaced apart from one another in the longitudinal direction, between wire coil and core wire. However, it is also conceivable in principle to do without a fluid-permeable connection. However, in the case of very narrow hollow organs, which generate a high degree of resistance upon movement of the guide wire, this may sometimes be disadvantageous, since there is the possibility of the wire coil being strongly compressed and/or expanded during the movement.

In particular, the fluid-permeable connection is present as an integrally bonded connection which is designed asymmetrically and/or to one side with respect to a longitudinal center axis of the wire coil, in particular a soldered connection, between wire coil and core wire. This has the effect that, in the area of the fluid-permeable connection, a channel-like passage lying to the side of the core wire remains free for the fluid that is to be delivered and/or withdrawn. Moreover, in a fluid-permeable connection designed in this way, no additional elements are required, which particularly reduces the amount of space needed and permits a correspondingly more compact construction of the guide wire.

The integrally bonded connection is in particular a soldered connection. However, it is also possible to provide an adhesive connection and/or a welded connection. In particular, several separate connection webs can be present, e.g. composed of a solder and/or an adhesive, which extend for example in a radial direction between core wire and wire coil. The connection webs then form a fluid-permeable connection, since the free spaces between the connection webs form a passage for fluid.

In another preferred embodiment, the fluid-permeable connection is designed as an integrally bonded connection, in particular as a soldered connection, wherein a tube extending parallel to the core wire and embedded in the integrally bonded connection is present as a channel-like passage for the fluid that is to be delivered and/or withdrawn. The integrally bonded connection can be designed, for example, as a soldered connection and/or adhesive connection. Because of the tube, the fluid-permeable connection has, on the one hand, a relatively precisely defined through-opening. On the other hand, it has been shown that a tube can be relatively easily embedded in the integrally bonded connection, which simplifies the production of the guide wire. In this case, the core wire, with the tube arranged alongside it, can be connected all the way round to the wire coil in an integrally bonded manner, which is usually easier than connecting the core wire on one side to the wire coil. Moreover, a more stable connection between core wire and wire coil is formed.

The core wire is advantageously fixed in the lumen at a distance in the proximal direction from the proximal end of the wire coil and, in particular, is arranged eccentrically with respect to a longitudinal axis of the lumen. In this way, the core wire extends from the proximal end of the wire coil, all the way through the latter, as far as the distal end or the guide-wire tip. It has been found that an arrangement of this kind is particularly advantageous since the abrupt change in elasticity normally found between the hollow shaft and the wire coil can be optimally compensated by the core wire. An eccentric arrangement of the core wire, bearing on a boundary surface of the lumen, also simplifies the production of the guide wire. If the core wire and the hollow shaft and also the boundary surface of the lumen are made of similar materials, e.g. metals, the core wire can, for example, be welded directly onto the boundary surface of the lumen.

However, it is also possible to provide a hollow shaft protruding into the wire coil and to arrange the core wire spaced apart in the distal direction from the proximal end of the wire coil. This may sometimes be advantageous for specific uses, although in this case a relatively substantial change in elasticity between hollow shaft and wire coil can occur.

The lumen and/or the wire coil preferably have a circular cross-sectional area, in particular with a maximum external diameter of the core wire being smaller than a minimum internal diameter of the lumen and/or smaller than a minimum internal diameter of the wire coil. Particularly preferably, the minimum internal diameter of the lumen and/or the minimum internal diameter of the wire coil is 3-4 times greater than the external diameter of the core wire in the area of the wire coil. In this way, a free space remains alongside the core wire along the entire length of the core wire in the lumen and/or in the wire coil, which free space can serve as a fluid channel (extending parallel to the longitudinal axis of the guide wire) for the fluid that is to be delivered and/or withdrawn. This represents a particularly simple measure for the design of a fluid channel and is advantageous from the point of view of production technology. Moreover, this permits a particularly compact construction of the guide wire, which in turn improves the insertability and the precise movement of the guide wire in a hollow organ.

However, a design of this kind is not absolutely essential. In principle, the core wire can also completely fill the lumen and/or the wire coil. In particular, in the interior of the core wire, it is possible, for example, to arrange passage channels via which the fluid to be delivered and/or withdrawn can be conveyed between the lumen and the distal inner area of the wire coil. If considered appropriate, it is likewise possible for at least one further longitudinally extending lumen to be arranged in the hollow shaft and/or on the outside of the hollow shaft in order to serve as a fluid channel for passage of the fluid that is to be delivered and/or withdrawn.

The core wire, the hollow shaft, the lumen and/or the wire coil do not necessarily have a circular cross section. For example, said elements of the guide wire can also have oval cross sections, if this appears appropriate. In these cases, the diameter is to be understood in particular as a maximum extent of the respective element in a transverse direction perpendicular to the longitudinal direction of the guide wire.

In order to generate the at least one opening, at least two adjacent windings of the wire coil are preferably arranged without touching and/or spaced apart from each other. Between the at least two adjacent windings, there is then advantageously a spacing that corresponds to 0.1-0.5 times a wire diameter of the wire coil. In particular, an opening of this kind opens out from the wire coil laterally or in the transverse direction. Particularly in the case of a wire coil made from a round wire, the opening is substantially entirely free of edges. This guarantees in particular a good insertability and positionability of the guide wire in a hollow organ, since the danger of the opening catching and/or sticking in the hollow organ is minimal. Moreover, the size or the surface area of the opening can be easily adjusted via the spacing between the adjacent windings forming the opening and/or via the number of spaced-apart windings. In this way, the opening can be adapted within wide ranges to very different requirements. Moreover, the guide wire can be made particularly compact, since no additional elements have to be arranged for the opening. In particular, a spacing of 0.1-0.5 times the wire diameter between the adjacent windings of an opening ensures sufficient permeability in combination with suitable elasticity of the wire coil made from a wide variety of metallic wire materials. To produce an opening, the wire coil can be soft-drawn at the desired location.

However, in addition to or instead of an opening between adjacent windings of the wire coil, it is also possible in principle, for example, to provide an opening in the guide-wire tip. This opening can, for example, be a longitudinally extending bore through the guide-wire tip. In this way, a fluid can be delivered and/or withdrawn directly in front of the guide-wire tip in the distal direction, which may be advantageous for specific requirements.

Moreover, for specific applications and/or in the case of specific wire materials, the spacing between the adjacent windings can also be less than 0.1 times or greater than 0.5 times the wire diameter of the wire coil.

In another preferred embodiment, several further adjacent windings of the wire coil are arranged bearing on one another, such that at least one fluid-tight portion of the wire coil is formed. In combination with the at least one opening, it is thus possible that the outlet and/or inlet for the fluid that is to be delivered and/or withdrawn can be provided at an exactly defined location of the wire coil. In this way, the delivery and/or withdrawal of the fluid can take place substantially at one point at an exactly located position in the hollow organ. It is thus possible, with a single wire coil, which can be composed of a single wire for example, to convey a fluid (without a membrane additionally having to be provided as a jacket or tubing) and also to remove or introduce the fluid through individual openings.

However, it is also possible for several or all of the windings of the wire coil to be spaced apart, such that the fluid can, for example, be delivered and/or withdrawn across the entire distal inner area of the wire coil or even along the entire length of the wire coil. Such designs of the wire coil can be advantageous in particular for administering drugs across a large surface area. It should of course be noted that a longer portion of spaced-apart windings does not lead to release or uptake of the fluid distributed along the entire length.

It is also possible in principle, and sometimes advantageous for certain uses, to provide a wire coil that is made up exclusively of windings bearing on one another. In this case, as has already been explained above, the at least one opening can be formed in the guide-wire tip, for example.

In a particularly preferred embodiment, several openings and several fluid-tight portions are present in the wire coil, and they are preferably arranged in an alternating sequence and in particular at regular intervals along an entire length of the wire coil. The individual openings are in particular of substantially the same size. In this way, a fluid can be locally delivered and/or withdrawn at several spaced-apart locations simultaneously. In particular, when delivering a fluid, this permits precise dosing.

In principle, however, the openings can also be present at irregular intervals, if this appears appropriate for specific uses.

The fluid-tight portions of the wire coil are preferably radiopaque. For this purpose, the wire coil is preferably made from a platinum wire, wherein a wire diameter is in particular at least 25 µm, preferably 45-55 µm. In this way, the fluid-tight portions, or the portions of the wire coil with windings bearing on one another, are radiopaque in the normally used imaging methods with X-rays and can be visualized directly. In this case, it is possible to do without additional X-ray markers on the guide wire. The position of the wire coil can thus be determined very exactly.

The openings of the wire coil that are formed by the spaced-apart windings are preferably radiolucent. This can be achieved in particular if a spacing between the at least two adjacent windings is 0.1-0.5 times the wire diameter of the wire coil. This permits direct visualization of the openings in the wire coil, as a result of which the precision with which a fluid is delivered and/or withdrawn is further improved. In the case of several radiolucent openings arranged at regular intervals, with radiopaque portions of the wire coil lying between them, it is possible to closely determine the position of the guide wire or the course of the hollow organ in three dimensions.

In principle, however, the fluid-tight portions of the wire coil can also be radiolucent and/or the openings radiopaque. If so desired, it is possible in these cases, for example, to arrange additional X-ray markers, e.g. metal rings, on the guide wire.

Moreover, an elasticity of the wire coil is preferably greater than an elasticity of the hollow shaft. In particular, a modulus of elasticity of the wire coil is less than a modulus of elasticity of the hollow shaft. In this way, a distal portion of the guide wire is more elastic than the areas of the guide wire lying behind it in the distal direction. In this way, the more elastic distal portion of the guide wire can be better steered through the in some cases strongly branched and curved hollow organs, e.g. blood vessels, while the rear portions have sufficient stiffness for pushing in the guide wire. All in all, the insertability and positionability of the guide wire are thereby improved. Fine adjustment of the elasticities in the distal area takes place, as has been explained above, through the core wire.

In principle, however, the elasticities of core wire and hollow shaft can also be identical for example, if this appears appropriate for specific uses.

Particularly preferably, the hollow shaft is present in the form of a steel tube, while the wire coil is made in particular from a platinum wire. A combination of this kind has proven particularly suitable in respect of good insertability in combination with precise positioning. Moreover, said steel and platinum are to a very large extent chemically inert to a great many fluids of interest in this context.

In principle, however, other materials can also be used for the hollow shaft and/or the wire coil. In particular, the hollow shaft can be made, for example, from a plastic tube.

It is also advantageous if the hollow shaft is designed in two or more parts, wherein a proximal portion of the hollow shaft preferably has less elasticity than a distal portion of the hollow shaft. A modulus of elasticity of the proximal portion is in particular greater than a modulus of elasticity of the distal portion of the hollow shaft. It is also preferable if the distal portion of the hollow shaft has less flexibility than the wire coil. In particular, the modulus of elasticity of the distal portion of the hollow shaft is greater than the modulus of elasticity of the wire coil. Advantageously, an external diameter of the hollow shaft made of two or more parts is substantially constant along an entire length of the hollow shaft. Correspondingly, an internal diameter of the hollow shaft made of two or more parts is advantageously substantially constant along an entire length of the hollow shaft.

Guide wires of this kind have, in particular, an elasticity that increases toward the guide-wire tip. By means of the hollow shaft being made up of two or more parts, the increase in elasticity in the longitudinal direction can extend over a longer area than in the case of a one-part hollow shaft. It is thus possible to further improve the insertability and positionability of the guide wire in a hollow organ.

In a hollow shaft made up of two or more parts, the core wire is preferably mounted in the proximal portion of the hollow shaft, with the core wire extending in particular through the distal portion of the hollow shaft and the wire coil as far as the guide-wire tip. In this way, the increase in elasticity of the guide wire in the longitudinal direction can be controlled particularly exactly, and abrupt changes in elasticity at the transitions between the various areas of the hollow shaft and the wire coil can be compensated if necessary.

In principle, however, one-part hollow shafts can also be used. It is also possible for hollow shafts made up of two or more parts to be provided which, for example, have substantially the same elasticties in their distal and proximal portions. If so desired, an elasticity can be controlled in these cases via the core wire, for example. Likewise, the external and/or internal diameters of the hollow shaft can be designed decreasing in the distal direction for example.

It is particularly preferable that a diameter of the core wire decreases from a proximal end of the core wire toward a distal end of the core wire, preferably such that a flexibility of the guide wire decreases continuously from the proximal end of the core wire toward the guide-wire tip. In particular, this is independent of whether the hollow shaft is made up of one, two or more parts.

If appropriate, however, the core wire can also be designed differently.

In a preferred variant, the proximal portion consists of a metal tube, in particular a steel tube, and/or the distal portion consists of a plastic tube, in particular a polyimide tube. A combination of this kind has proven particularly advantageous in respect of good insertability together with precise positionability.

Moreover, said materials are to a very large extent chemically inert to a great many fluids of interest in this context.

For specific uses, however, other materials or structures of the hollow shaft may also be advantageous.

The several parts preferably have the same external diameter. That is to say, there are no steps at the transitions. According to this design option, therefore, the proximal portion (e.g. the steel tube) and the distal portion (e.g. the individual wire coil) and the intermediate tube (plastic tube) connecting them have the same external diameter. Advantageously, the internal diameter is also substantially the same size. Moreover, in the variants just described, it is particularly advantageous in each case if the tubular part of the guide wire is composed exclusively of the three parts with the same external diameter and is free of an additional membrane (envelope).

A particularly preferred embodiment is therefore characterized in that the wire coil is composed of a single wire, that the area of the wire coil is free of an additional membrane, and that precisely three different tubular parts are provided with substantially the same external diameter.

It can also be advantageous if a hollow cylindrical tubular stub, surrounding the core wire and protruding from a distal end of the hollow shaft, extends partially into the interior of the wire coil. A distal end of the tubular stub is spaced apart in the proximal direction from the distal end of the wire coil. In this way, the wire coil can be additionally supported at the transition to the hollow shaft, which in particular increases the stability of the connection and reduces the change in elasticity at the transition. Because of the distal end of the tubular stub arranged spaced apart from the guide-wire tip, it is also possible for fluid to be delivered and/or withdrawn via an opening formed laterally in the wire coil directly behind the guide-wire tip. If the tubular stub extends as far as the guide-wire tip, a fluid can be delivered and/or withdrawn, for example, via an opening formed in the longitudinal direction in the guide-wire tip.

However, a stub of this kind is not absolutely essential and, accordingly, can also be omitted or modified.

An external diameter of the tubular stub preferably corresponds approximately to an internal diameter of the wire coil. An optimal support of the wire coil is achieved in this way. Moreover, an internal diameter of the tubular stub is preferably larger than an external diameter of the core wire in the area of the tubular stub. In this way, a free space remains alongside the core wire and serves as a fluid channel for passage of the fluid that is to be delivered and/or withdrawn. This is a solution that is particularly compact and that is advantageous from the point of view of production technology.

In principle, however, it is also conceivable to depart from the diameters cited above. If the chosen internal diameter of the tubular stub is approximately identical to the external diameter of the core wire in this area, a fluid channel can be formed, as had already been explained above, for example in the core wire and/or in a separate fluid channel alongside the tubular stub.

The tubular stub is connected more preferably on the inside to the core wire via a fluid-permeable connection and on the outside to the wire coil via a further connection. In this way, a still more precise movement of the guide wire in a hollow organ is possible in particular, since compressions and/or expansions of the wire coil in the longitudinal direction are almost completely prevented. As has already been described above, the fluid-permeable connection can be an integrally bonded connection that is designed asymmetrically and/or to one side, in particular a soldered connection between tubular stub and core wire. It is likewise possible to embed an additional tube in the fluid-permeable connection. In this way, in the area of the fluid-permeable connection, a channel-like passage to the side of the core wire remains free for the fluid that is to be delivered and/or withdrawn. The further connection between tubular stub and wire coil can be present, for example, as an integrally bonded connection, in particular a welded connection, an adhesive connection and/or a soldered connection.

However, it is also possible to do without fluid-permeable connections of this kind and/or further connections.

The guide-wire tip of the guide wire is present in particular as a rounded attachment on the distal end of the wire coil. Hemispherical attachments have proven particularly suitable as guide-wire tips. Attachments of this kind as guide-wire tips are particularly atraumatic. For example, the guide-wire tips are produced from a plastic material.

However, other shapes of guide-wire tips are also possible, if this is deemed necessary or advantageous for specific uses. The guide-wire tip does not necessarily have to be present as a separate part and/or attachment. It may sometimes also be advantageous for specific uses if the distal end of the wire coil is designed as a guide-wire tip. In this case, guide-wire tip and wire coil can be designed as one piece, for example.

The guide wires according to the invention can be used in particular for diagnostic and/or therapeutic purposes on the human and/or animal body. Specifically, the guide wires according to the invention can be used, for example, for the treatment of peripheral arterial occlusive disease or coronary heart disease, for recanalization of blood vessels, for flow-improving treatment in degenerated bypass vessels, for drug therapy of tumors and/or for pressure measurement in a hollow organ of the human and/or animal body. However, other uses are also possible.

A further aspect of the invention relates to a method for the diagnostic and/or therapeutic treatment of vessels and/or tumors. In this method, a distal portion of a guide wire according to the invention is inserted into a vessel, the guide-wire tip is positioned at a location to be treated in the vessel and/or in the area of a tumor, and a fluid active substance is then introduced through the lumen of the hollow shaft and the at least one opening of the guide wire into the vessel and/or tumor to be treated.

The release of the fluid active substance can take place for seconds or a period of some hours and is primarily dependent on the clinical indication. The flow speed, and therefore also the amount of substance released, is mainly dependent on the pressure applied to the fluid active substance at the proximal end of the guide wire and on the substance properties of the administered fluid active substance.

By virtue of the exact positionability of the guide wire according to the invention, the insertion of a guide wire according to the invention into a vessel and/or a tumor and the administration of a fluid active substance locally and/or at one point can have a considerable and very precisely predictable efficacy.

The fluid active substance is, for example, a contrast agent for an imaging procedure, a thrombolytic substance, and/or a substance with an anti-platelet, embolic, toxic and/or anti-proliferative effect.

Representatives of thrombolytic substances are, for example, rt-PA, Metalyse, streptokinase and/or urokinase. Also suitable as fluid active substances are, for example, combinations of substances with anti-platelet and anti-plasma effects. Here, it is possible in particular to use aspirin, clopidogrel, Efficient or the group of GPIIb/IIIA antagonists. As substances with an anti-proliferative effect, it is possible, for example, to use paclitaxel, tacrolimus, sirolimus and/or everolimus. However, depending on the treatment method, other active substances can also be used.

During the recanalization of vessels in the acute stage of infarction, no-reflow phenomena often occur following ischemia, which phenomena are caused mainly by a peripheral thromboembolism and/or a thrombotic peripheral vascular occlusion. Systemic thrombolytic therapy is sometimes not possible in order to break up the clots, since these are old clots which are either not reached by the thrombolytic substance or which, because they are old, cannot be broken up. The insertion of a guide wire according to the invention into the periphery of such a vessel and the local administration of, for example, thrombolytic substances, such as rt-PA, Metalyse, streptokinase and/or urokinase, can develop thrombolytic efficacy by virtue of the at least one opening of the guide wire according to the invention being in immediate proximity to the thrombotic structure. A further improvement of the antegrade flow can also be expected through a combination of substances with an anti-platelet and anti-plasma effect. These include, in particular, aspirin, clopidogrel, Effient or the group of GPIIb/IIIa antagonists.

Degenerated bypass vessels, which likewise show arteriosclerotic changes along an extended vessel process and are occupied by clots, likewise have a tendency to no-reflow phenomena. Here too, the insertion of a guide wire according to the invention and the release of substances with an anti-plasma or anti-platelet effect can provide a possible improvement in flow.

Patients with a diffuse vascular condition involving peripheral arterial occlusive disease or coronary heart disease can only be treated to a limited extent with current interventional techniques. It is to be expected here that an influence on the lumen width can be achieved by insertion of a guide wire according to the invention and by release of anti-proliferative substances such as paclitaxel, tacrolimus, sirolimus and/or everolimus.

Special tumors that have clearly defined blood supplies and that cannot be removed, or that can be removed only by placing the patient at increased surgical risk or by causing considerable damage to the otherwise healthy state of the patient, can be treated with drugs by intravascular insertion of a guide wire according to the invention. Substances that can be used here are of an embolic, toxic and anti-proliferative nature.

Further advantageous embodiments and feature combinations of the invention follow from the following detailed description and from the patent claims taken in their entirety.

BRIEF DESCRIPTION OF THE DRAWINGS

In the drawings used to explain the illustrative embodiment.

In principle, identical parts in the figures are provided with identical reference signs.

WAYS OF IMPLEMENTING THE INVENTION

Figure 1:
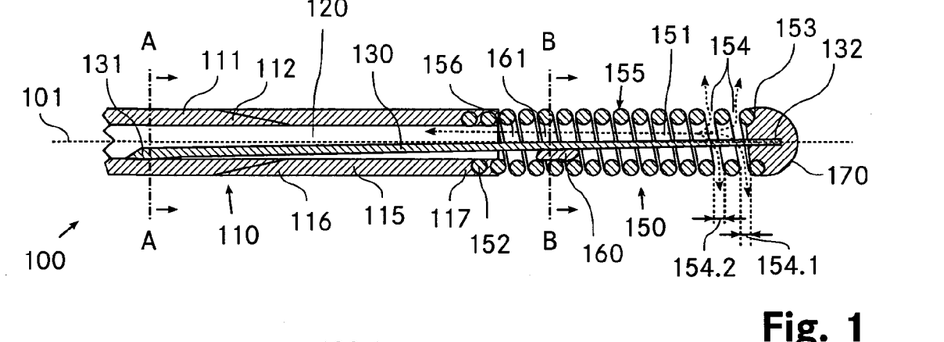
FIG. 1 shows a longitudinal section through a first guide wire according to the invention, with a through-opening lying directly behind the guide-wire tip in a wire coil, and with a fluid-permeable connection between core wire and wire coil.
Figure 2:
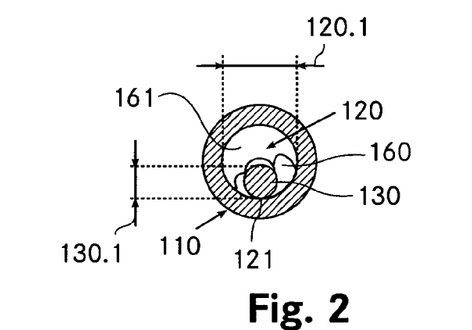
FIG. 2 shows the guide wire from FIG. 1 in the transverse section along the line A-A.
Figure 3:
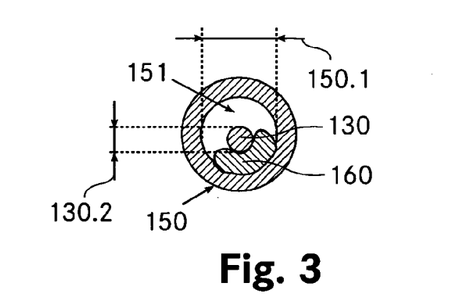
FIG. 3 shows the guide wire from FIG. 1 in the transverse section along the line B-B.

FIGS. 1-3 show a first guide wire 100 according to the invention, with FIG. 1 showing a longitudinal section along a longitudinal center axis 101 of the first guide wire 100. The guide wire 100 comprises a two-part hollow shaft 110, wherein a proximal portion 111 of the hollow shaft 110 is made, for example, from a hollow cylindrical steel tube, while a distal portion 115 is made from a hollow cylindrical polyimide tube arranged coaxially with respect to the proximal portion 111. A transverse section through the proximal portion 111 of the hollow shaft 110 is shown in FIG. 2. Because of the choice of material, the elasticity of the distal portion 115 of the hollow shaft 110 is greater than the elasticity of the proximal portion 111.

The distal end 112 of the proximal portion 111 tapers in the distal direction with a constant internal diameter, whereas the proximal end 116 of the distal portion 115 widens conically with a constant external diameter in the proximal direction in a manner complementary to the distal end 112 of the distal portion 111. The internal diameters and also the external diameters of the two portions 111, 115 are substantially the same size, such that a continuous circular cylindrical lumen 120 with a constant diameter 120.1 is present in the hollow shaft 110.

From the distal end 117 of the distal portion 115, a coaxially arranged hollow cylindrical wire coil 150 extends in the distal direction away from the hollow shaft 110. The proximal end 152 of the wire coil 150 is anchored in the distal end 117 of the distal portion 115 by pressure welding. The wire coil is made, for example, from a platinum wire with a wire diameter of ca. 50 μm. A transverse section through the wire coil 150 is shown in FIG. 3. A flexibility of the wire coil 150 is greater than the flexibility of the distal portion 115 of the hollow shaft 110.

A guide-wire tip 170 in the form of an atraumatically rounded and hemispherical attachment made of plastic is mounted on the distal end 153 of the wire coil. The guide-wire tip 170 can be connected to the wire coil 150, for example by pressure welding.

The first and second windings of the wire coil 150, and the second and third windings thereof, arranged directly in succession in the proximal direction behind the guide-wire tip 170 are spaced apart such that, in the area of the guide-wire tip, a fluid-permeable through-opening 154 is present in the wire coil 150. A first spacing 154.1 between the first and second windings, and a second spacing 154.2 between the second and third windings, corresponds in each case approximately to 0.3 times a wire diameter of the wire coil 150.

The through-opening 154 opens directly into the distal inner area 151 of the wire coil 150 adjoining the guide-wire tip 170 in the proximal direction. In other words, the distal inner area 151 of the wire coil 150 thus has an outwardly open through-opening 154 for a fluid that is to be introduced and/or removed. The other windings of the wire coil 150 are arranged bearing directly on one another and form a fluid-tight and radiopaque portion 155 of the wire coil 150.

An internal diameter 150.1 of the wire coil 150 is substantially constant along the entire length and corresponds approximately to an internal diameter of the hollow shaft 110 or to a diameter of the hollow cylindrical lumen 120.

In the proximal portion 111 of the hollow shaft 110, the proximal end 131 of a core wire 130 is also welded on the boundary surface of the lumen 120 or in the interior of the hollow shaft 110. The proximal end 131 of the core wire 130 is arranged eccentrically in the hollow shaft 110. The core wire 130 extends through the distal portion 115 and the wire coil 130 as far as the guide-wire tip 170. The distal end 132 of the guide wire 130 is connected to the guide-wire tip 170, for example by pressure welding.

The core wire 130 is made, for example, from steel and has an external diameter decreasing from its proximal end 131 to its distal end 132, wherein a proximal external diameter 130.1 at the proximal end 131 of the core wire 130 is greater than a distal external diameter 130.2 of the core wire in the area of the wire coil 150. A flexibility of the guide wire 100 decreases substantially continuously from the proximal end 131 of the core wire 130 toward the guide-wire tip 170.

The external diameter 130.1, 130.2 of the core wire 130 is without exception smaller than a diameter 120.1 of the lumen 120 and smaller than an internal diameter 150.1 of the wire coil 150.

In a proximal portion of the wire coil 150, the core wire 130 is connected to the wire coil 150 via a fluid-permeable connection 160. The fluid-permeable connection 160 is, for example, an integrally bonded connection in the form of a soldered connection. The fluid-permeable connection 160 is designed asymmetrically or to one side with respect to the longitudinal center axis 101 of the guide wire 100, such that, in the area of the fluid-permeable connection 160, a channel-like passage 161 alongside the core wire 130 remains free for the fluid that is to be delivered and/or withdrawn. The distal inner area 151 of the wire coil 150 thus communicates via the channel-like passage 161 with a proximal inner area 156 of the wire coil 150. In the transverse section, the fluid-permeable connection covers about 40% of the cross-sectional span of the inner area of the wire coil 150. The internal diameter 150.1 of the wire coil 150, in the area of the fluid-permeable connection 160, is ca. 3.5 times greater than the proximal external diameter 130.1 of the core wire 130 in this area.

Thus, the lumen 120 of the first guide wire 100 communicates with the distal inner area 151 of the wire coil 150 via the channel-like passage 161 formed alongside the core wire 130, wherein the distal inner area 151 in turn has a through-opening 154 toward the outside for delivering and/or withdrawing a fluid.

Figure 4:
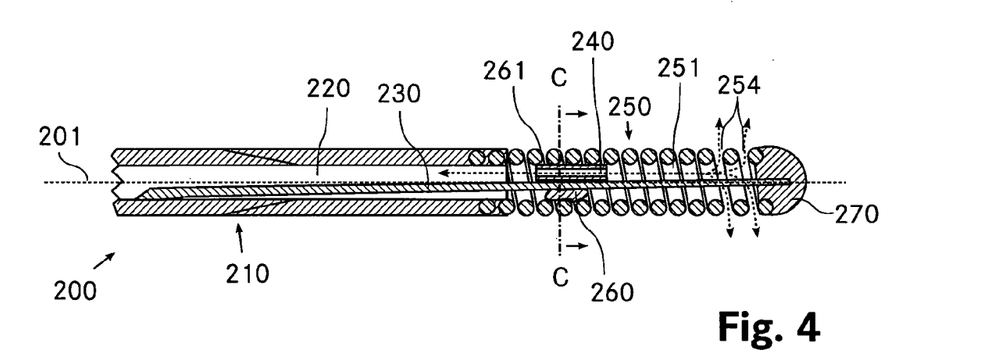
FIG. 4 shows a longitudinal section through a second guide wire according to the invention, with a fluid-permeable connection in the form of an embedded tube.
Figure 5:
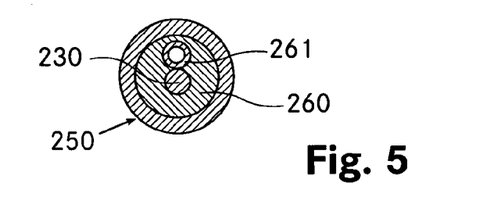
FIG. 5 shows the guide wire from FIG. 4 in the transverse section along the line C-C.

FIG. 4 shows a second guide wire 200 according to the invention in a longitudinal section along its longitudinal center axis 201, while FIG. 5 shows a transverse section in the area of the fluid-permeable connection 260 of the second guide wire.

The second guide wire 200 likewise has a hollow shaft 210 with a lumen 220, wherein the hollow shaft 210 and the lumen 220 of the second guide wire 200 are substantially identical to the hollow shaft 100 and the lumen 120 of the first guide wire 100. Likewise, the second guide wire 200 has a wire coil 250 secured on the hollow shaft 210, with a guide-wire tip 270 and a core wire 230. The wire coil 250, the guide-wire tip 270 and the core wire 230 are also substantially identical to the corresponding parts of the first guide wire 100. Moreover, said parts of the second guide wire 200 are arranged in the same way and secured to one another in the same way as the corresponding parts of the first guide wire 100. Accordingly, the wire coil 250 of the second guide wire 200 also has a through-opening 254 arranged directly behind the guide-wire tip 270 for a fluid that is to be delivered and/or withdrawn.

In contrast to the first guide wire 100, however, the second guide wire 200 has a fluid-permeable connection 260 designed as an integrally bonded connection with a tube 261 embedded therein and extending parallel to the core wire as a channel-like passage for the fluid that is to be delivered and/or withdrawn. The tube 261 is, for example, embedded all the way round in an integrally bonded manner in a solder composition and connected to the wire coil 250.

Thus, the lumen 220 of the second guide wire 200 communicates with the distal inner area 251 of the wire coil 250 via the tube 161, which serves as channel-like passage and is arranged alongside the core wire 230, wherein the distal inner area 251 once again has the through-opening 254 for delivering and/or withdrawing a fluid.

Figure 6:
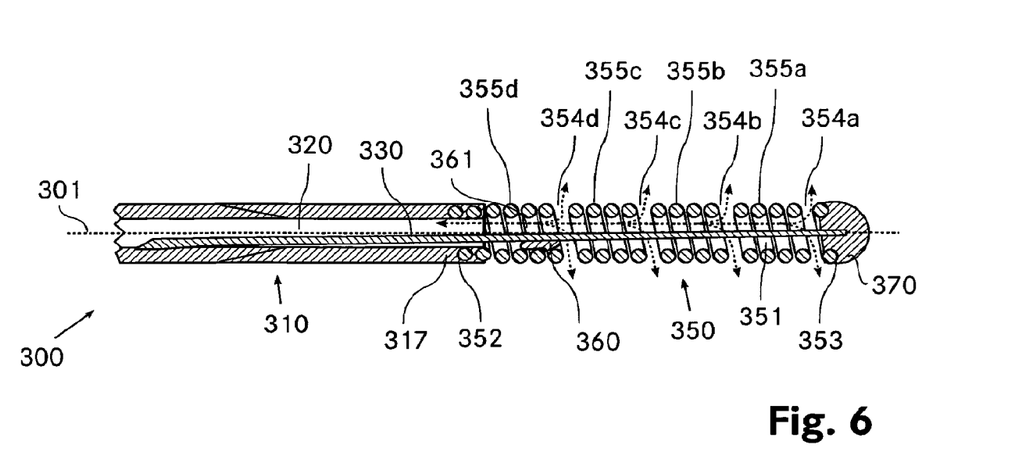
FIG. 6 shows a longitudinal section through a third guide wire according to the invention, with several through-openings spaced apart from one another in the wire coil.

FIG. 6 shows a third guide wire 300 according to the invention in a longitudinal section along its longitudinal center axis 301.

The third guide wire 200 likewise has a hollow shaft 310 with a lumen 320, wherein the hollow shaft 310 and the lumen 320 of the third guide wire 300 are substantially identical to the hollow shaft 100 and the lumen 120 of the first guide wire 100. Likewise, the third guide wire 300 has a wire coil 350 secured on the hollow shaft 310, with a guide-wire tip 370 and a core wire 330. The wire coil 350 is likewise made, for example, from a platinum wire with a diameter of ca. 50 μm.

In contrast to the first guide wire 100, however, the wire coil 350 has several through-openings 354a, 354b, 354c, 354d spaced apart from one another. The first and second windings of the wire coil 350 lying directly behind the guide-wire tip 370 in the proximal direction are spaced apart from one another such that, in the area of the guide-wire tip 370, a first fluid-permeable and radiolucent through-opening 354a is present in the wire coil 150.

In the proximal direction, a first fluid-tight and radiopaque portion 355a of the wire coil 350 adjoins the first fluid-permeable through-opening 354a. The first fluid-tight portion 355a is formed, for example, by four windings of the wire coil 350 bearing directly on one another.

In the proximal direction, the first fluid-tight portion 355a is followed by a second fluid-permeable and radiolucent through-opening 354b, which is formed by two spaced-apart windings of the wire coil 350. It is followed in the proximal direction by a second fluid-tight and radiopaque portion 355b of the wire coil 350. Like the first fluid-tight area 355a, the second fluid-tight area 355b is also formed, for example, by four windings of the wire coil 350 bearing directly on one another.

In the proximal direction, the second fluid-tight portion 355b is followed by a third fluid-permeable and radiolucent through-opening 354c, which is again formed by two spaced-apart windings of the wire coil 350. The third through-opening is followed in the proximal direction by a third fluid-tight and radiopaque portion 355c, which is likewise formed by four windings of the wire coil 350 bearing directly on one another.

In the proximal direction, the third fluid-tight portion 355c is followed directly by a fourth fluid-permeable and radiolucent through-opening 354d formed by two spaced-apart windings of the wire coil 350.

The fourth fluid-permeable through-opening 354d is adjoined in the proximal direction by a fourth fluid-tight and radiopaque portion 355d of the wire coil 350 formed by four windings of the wire coil bearing directly on one another.

The last wire windings of the wire coil 350 in the proximal direction, which form the proximal end 352 of the wire coil, are welded in the distal end 317 of the hollow shaft 310.

Thus, along the entire length of the wire coil 350, several fluid-permeable and radiolucent through-openings 354a, 354b, 354c, 354d are spaced regularly apart from one another and a separated by several fluid-tight and radiopaque portions 355a, 355b, 355c, 355d. The spaced-apart through-openings 354a, 354b, 354c, 354d each have, for example, a width which, measured in a direction parallel to the longitudinal center axis 301, is ca. 0.5 times the wire diameter of the wire coil 350.

In the area of the fourth fluid-tight portion 355d, the core wire 370 protruding from the hollow shaft 310 and extending through the wire coil 350 as far as the guide-wire tip is connected to the wire coil 350 via a fluid-permeable connection 360. The fluid-permeable connection 360 has substantially the same design as the fluid-permeable connection 160 of the first guide wire 100 and is present, for example, as an integrally bonded connection in the form of a soldered connection. The fluid-permeable connection 360 is accordingly designed asymmetrically or to one side with respect to the longitudinal center axis 301 of the third guide wire 300, such that, in the area of the fluid-permeable connection 360, a channel-like passage 261 alongside the core wire 130 remains free for the fluid that is to be delivered and/or withdrawn. In the transverse section, the fluid-permeable connection covers about 40% of the cross-sectional span of the inner area of the wire coil 350. The internal diameter of the wire coil 350, in the area of the fluid-permeable connection 360, is ca. 3.5 times greater than the external diameter of the core wire 330 in this area.

Thus, the lumen 320 of the third guide wire 300 communicates with the distal inner area 351 of the wire coil 350 via the channel-like passage 361 formed alongside the core wire 330, wherein the distal inner area 351 again has the four through-openings 354a, 354b, 354c, 354d for delivering and/or withdrawing a fluid.

Figure 7:
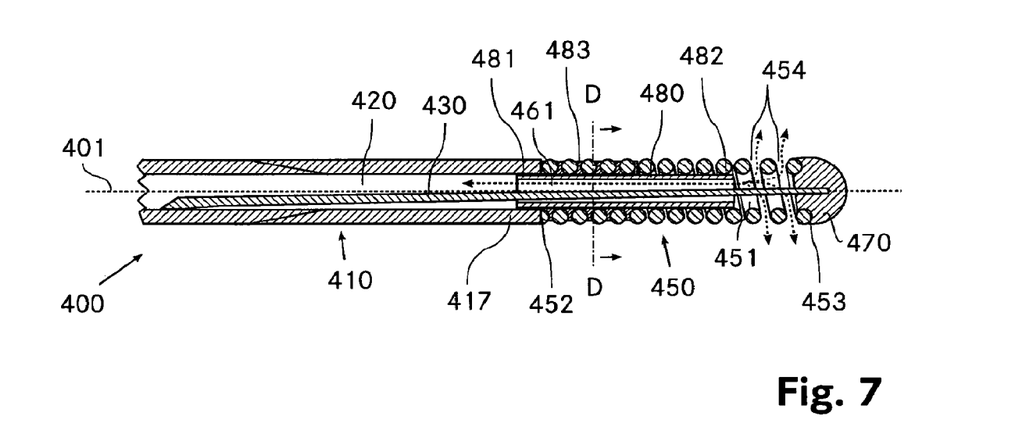
FIG. 7 shows a longitudinal section through a fourth guide wire according to the invention, with a tubular stub protruding from the hollow shaft into the wire coil.
Figure 8:
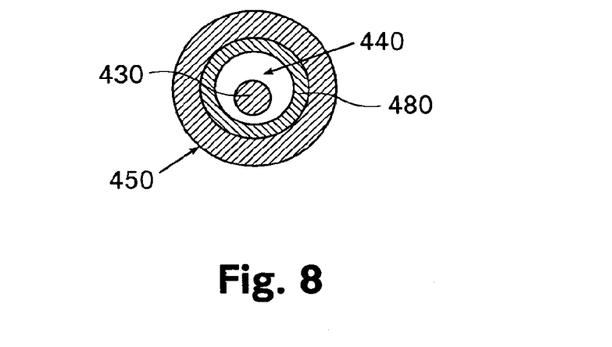
FIG. 8 shows the guide wire from FIG. 7 in the transverse section along the line D-D.

FIGS. 7 and 8 show a fourth guide wire 400 according to the invention in a longitudinal section along the longitudinal axis 401 and in a transverse section. The hollow shaft 410, the wire coil 450, the guide-wire tip 370 and the core wire 430 of the fourth guide wire 400 are substantially identical to the corresponding parts of the first guide wire 100. Accordingly, the wire coil 450 has a fluid-permeable through-opening 454 which is arranged directly behind the guide-wire tip 370 in the proximal direction and which is formed by three spaced-apart windings of the wire coil and communicates with the distal inner area 451 of the wire coil. The through-opening 454 of the fourth wire coil 450 corresponds substantially to the through-opening 151 of the first guide wire 100.

In contrast to the first guide wire 100, however, the fourth guide wire 400 additionally has a tubular stub 480 in the form of a hollow cylindrical tube which, coaxially with respect to the longitudinal center axis 401 of the fourth guide wire 400, protrudes from the hollow shaft 410 into the inner area of the wire coil 450. A proximal end 481 of the tubular stub 480 is anchored in a distal end 417 of the hollow shaft 410, e.g. by adhesive bonding and/or welding. The external diameter of the tubular stub 480 corresponds substantially to the internal diameter of the hollow shaft 410 and to the internal diameter of the wire coil 450.

A proximal portion of the tubular stub 480 is connected, for example by an adhesive connection, to the proximal portion of the wire coil 450.

A distal end of the tubular stub 480 is arranged in the distal direction directly in front of the through-opening 454, such that the through-opening 454 is not covered by the tubular stub 480 and thus remains free.

The core wire 430 of the fourth guide wire 400 extends through the tubular stub 480, wherein an internal diameter of the tubular stub 480 is without exception smaller than an external diameter of the core wire 430 in this area. Thus, a channel-like passage 461, through which a fluid to be delivered and/or withdrawn can pass, remains free in the tubular stub 480 alongside the core wire 430.

Thus, by way of the channel-like passage 461 present in the tubular stub 480, the lumen 420 of the fourth guide wire 400 communicates with the distal inner area 451 of the wire coil 450, which again has a fluid-permeable through-opening 454 for delivering and/or withdrawing a fluid.

Figure 9:
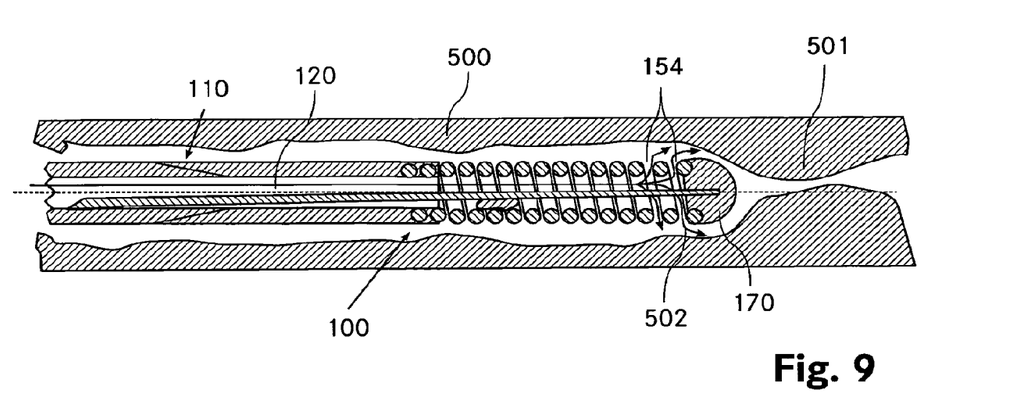
FIG. 9 shows a longitudinal section through the guide wire from FIG. 1 when inserted into a narrowed blood vessel.

FIG. 9 shows the first guide wire 100 from FIGS. 1-3 after it has been pushed into a blood vessel 500. The guide-wire tip 170 lies directly in front of a narrowed location 501 in the blood vessel 500, which is to be treated, for example, by drugs. In the area of the proximal end of the guide wire 100 lying outside the body (and not shown in FIG. 9), the drug 502 to be administered can be introduced into the lumen 120 and can be fed into the vessel 500 via the through-opening 154 lying directly behind the guide-wire tip 170. Since the through-opening 154 lies directly in the area of the guide-wire tip 170, the drug to be administered passes relatively precisely into the area of the constriction 501 that is to be treated.

The embodiments described above are to be understood merely as illustrative examples, which can be modified in any desired way within the context of the invention.

Thus, in all of the guide wires 100, 200, 300, 400, it is possible, for example, to replace the two-part hollow shafts 110, 210, 310, 410 with one-part hollow shafts. These can be present, for example, in the form of a steel tube. In this case, the wire coil can be welded onto the front face of the hollow shaft, for example. It is also possible, of course, to use multi-part hollow shafts with three, four or more separate subsidiary portions. Regardless of whether they are in one, two or more parts, the hollow shafts 110, 210, 310, 410 can also be designed tapering in the distal direction for example, in order in particular to improve the insertability.

The distal end area 112 of the proximal portion 111 and/or the proximal end area 116 of the distal portion 115 of the hollow shaft 100 can also be differently designed and/or connected. For example, the two portions 111, 115 can be joined together in abutment, via in each case an annular front face lying perpendicularly with respect to the longitudinal center axis 101, and adhesively bonded and/or welded.

Likewise, the guide-wire tips 170, 270, 370, 470 can also be differently designed and, for example, adapted to a specific purpose.

In addition to the fluid-permeable connections 160, 260, 360, further connections can also be formed between core wire 130, 230, 330 and wire coil 150, 250, 350. However, it is also possible in principle to do completely without the fluid-permeable connections 160, 260, 360. Likewise, in the fourth guide wire 400, an additional fluid-permeable connection can be formed between core wire and tubular stub 480, for example in order to additionally increase the stability of the wire coil.

In the fluid-permeable connection 260 of the second guide wire 200, further tubes can also be present in addition to the tube 261, for example in order to increase the fluid-permeable cross-sectional surface area.

It is also possible in principle for the wire coils 150, 250, 350, 450 to be designed tapering in the distal direction toward the guide-wire tips if this appears appropriate. In some circumstances, this can improve the insertability of the guide wires.

In the third guide wire 300, it is also possible to provide more or fewer through-openings than the four through-openings 354a, 354b, 354c, 354d of the wire coil 450. It is thus conceivable, for example, for all of the windings of the wire coil 450 to be spaced apart, such that a fluid can be delivered and/or withdrawn along the entire length of the wire coil. A corresponding design is also possible in the wire coils 150, 250 of the first two guide wires 100, 200.

In the first guide wire 100, the proximal end 131 of the core wire 130 can in principle also be mounted in the distal portion 115 of the hollow shaft 110. The core wire 130 can also have areas with external diameters decreasing and/or increasing in stages, for example in order to compensate for abrupt changes in elasticity. In principle, however, the core wire can also have an external diameter that is constant along the entire length.

All of the guide wires 100, 200, 300, 400 can also be designed, for example, with an oval cross section, if this is advantageous for certain uses.

It is also possible to provide additional through-openings on the hollow shafts 110, 210, 310, 410 themselves, if this appears appropriate.

It can be stated in conclusion that novel guide wires have been created that can be inserted easily into human and/or animal hollow organs and that also permit highly precise and targeted introduction and/or removal of fluids at defined locations in human and/or animal hollow organs.

The invention claimed is:

1. A guide wire for a catheter, designed to introduce and/or remove fluids in human and/or animal hollow organs such as in blood vessels, comprising
   a) an elongate hollow shaft with a lumen for delivering and/or withdrawing the fluid, and
   b) an insertion aid in the form of a flexible wire coil attached coaxially to a distal end of the hollow shaft, with a guide-wire tip arranged at a distal end of the wire coil,
   c) a core wire being arranged in the lumen of the hollow shaft in order to control a flexibility of the guide wire, which core wire extends out of the lumen in a longitudinal direction and right through the wire coil to the guide-wire tip,
   d) a distal inner area of the wire coil, adjacent to the guide-wire tip in a proximal direction, communicating with the lumen of the hollow shaft via a fluid channel formed alongside the core wire and
   e) at least one outwardly open through-opening of the wire coil for the fluid that is to be introduced and/or removed,
   f) wherein the at least one through-opening is formed by at least two adjacent windings of the wire coil arranged spaced apart from each other,
   g) several further adjacent windings of the wire coil being arranged bearing on one another and thus forming at least one fluid-tight portion of the wire coil,
   h) and wherein a hollow cylindrical tubular stub, surrounding the core wire and protruding from a distal end of the hollow shaft, extends partially into the interior of the wire coil.

2. The guide wire as claimed in claim 1, characterized in that a fluid-permeable connection between wire coil and core wire is present in an area of a proximal end of the wire coil, such that the wire coil is mechanically fixed relative to the core wire, and the distal inner area of the wire coil communicates with a proximal inner area of the wire coil lying proximally from the fluid-permeable connection.

3. The guide wire as claimed in claim 2, characterized in that the fluid-permeable connection is present as an integrally bonded connection which is designed asymmetrically or to one side with respect to a longitudinal center axis of the wire coil between wire coil and core wire, such that, in the area of the fluid-permeable connection, a channel-like passage lying to the side of the core wire remains free for the fluid that is to be delivered and/or withdrawn.

4. The guide wire as claimed in claim 2, characterized in that the fluid-permeable connection is designed as an integrally bonded connection, wherein a tube extending parallel to the core wire and embedded in the integrally bonded connection is present as a channel-like passage for the fluid that is to be delivered and/or withdrawn.

5. The guide wire as claimed in claim 1, characterized in that the core wire is fixed in the lumen at a distance in the proximal direction from the proximal end of the wire coil and is arranged bearing on a boundary surface of the lumen, eccentrically with respect to a longitudinal axis of the lumen.

6. The guide wire as claimed in claim 1, characterized in that an external diameter of the core wire is smaller than an internal diameter of the lumen and/or smaller than an internal diameter of the wire coil, wherein the internal diameter of the lumen and/or the internal diameter of the wire coil is greater than the external diameter of the core wire in the area of the wire coil.

7. The guide wire as claimed in claim 1, characterized in that, in order to generate the at least one through-opening between the at least two adjacent windings, there is in particular a spacing that corresponds to 0.1-0.5 times a wire diameter of the wire coil.

8. The guide wire as claimed in claim 1, characterized in that several through-openings and several fluid-tight portions are present, which are preferably arranged in an alternating sequence and in particular at regular intervals along an entire length of the wire coil.

9. The guide wire as claimed in claim 1, characterized in that an elasticity of the wire coil is greater than an elasticity of the hollow shaft.

10. The guide wire as claimed in claim 1, characterized in that the hollow shaft is present in the form of a steel tube, and the wire coil is made from a platinum wire.

11. The guide wire as claimed in claim 1, characterized in that the hollow shaft is designed in two or more parts, wherein a proximal portion of the hollow shaft has less elasticity than a distal portion of the hollow shaft.

12. The guide wire as claimed in claim 11, characterized in that the proximal portion consists of a metal tube, in particular a steel tube, and/or the distal portion consists of a plastic tube, in particular a polyimide tube.

13. The guide wire as claimed in claim 11, characterized in that the distal portion of the hollow shaft has less flexibility than the wire coil.

14. The guide wire as claimed in claim 1, characterized in that a distal end of the tubular stub is spaced apart in the proximal direction from the distal end of the wire coil.

15. The guide wire as claimed in claim 14, characterized in that an external diameter of the tubular stub corresponds approximately to an internal diameter of the wire coil, and an internal diameter of the tubular stub is preferably larger than an external diameter of the core wire in the area of the tubular stub.

16. The guide wire as claimed in claim 1, characterized in that a diameter of the core wire decreases from a proximal end toward a distal end, preferably such that a flexibility of the guide wire increases continuously from the proximal end of the core wire toward the guide-wire tip.

17. The guide wire as claimed in claim 1, characterized in that the guide-wire tip is present as a rounded attachment on the distal end of the wire coil and is produced from a plastic material.

18. The guide wire as claimed in claim 1, characterized in that the wire coil consists of a single wire, in that the area of the wire coil is free of an additional membrane, and in that exactly three different tubular parts are provided with substantially the same external diameter.

19. A method for the diagnostic and/or therapeutic treatment of vessels and/or tumors, wherein a distal portion of the guide wire as claimed in claim 1 is inserted into a vessel, the guide-wire tip is positioned at a location to be treated in the vessel, and a fluid active substance is then introduced through the lumen of the hollow shaft and the at least one through-opening of the guide wire into the vessel to be treated, wherein the fluid active substance is a contrast agent for an imaging procedure, a thrombolytic substance, and/or a substance with an anti-platelet, embolic, toxic and/or anti-proliferative effect.

20. A guide wire for a catheter, designed to introduce and/or remove fluids in human and/or animal hollow organs such as in blood vessels, comprising
   a) an elongate hollow shaft with a lumen for delivering and/or withdrawing the fluid, and
   b) an insertion aid in the form of a flexible wire coil attached coaxially to a distal end of the hollow shaft, with a guide-wire tip arranged at a distal end of the wire coil,
   c) a core wire being arranged in the lumen of the hollow shaft in order to control a flexibility of the guide wire, which core wire extends out of the lumen in a longitudinal direction and right through the wire coil to the guide-wire tip,
   d) a distal inner area of the wire coil, adjacent to the guide-wire tip in a proximal direction, communicating with the lumen of the hollow shaft via a fluid channel formed alongside the core wire and
   e) at least one outwardly open through-opening of the wire coil for the fluid that is to be introduced and/or removed,
   f) wherein the hollow shaft is designed in two or more parts, wherein a proximal portion of the hollow shaft has less elasticity than a distal portion of the hollow shaft, and
   g) wherein the proximal portion consists of a metal tube and the distal portion consists of a plastic tub;
   h) and wherein a hollow cylindrical tubular stub, surrounding the core wire and protruding from a distal end of the hollow shaft, extends partially into the interior of the wire coil.

21. The guide wire as claimed in claim 20, characterized in that a distal end of the proximal portion tapers in a distal direction while an internal diameter stays constant, whereas a proximal end of the distal portion widens conically in the proximal direction in a manner complementary to the distal end of the distal portion while an external diameter stays constant, wherein the internal diameter and also the external diameter of the two portions are substantially the same size, providing a continuous circular cylindrical lumen with a constant diameter.

22. The guide wire as claimed in claim 20, characterized in that a distal end of the tubular stub is spaced apart in the proximal direction from the distal end of the wire coil.

23. The guide wire as claimed in claim 22, characterized in that an external diameter of the tubular stub corresponds approximately to an internal diameter of the wire coil, and an internal diameter of the tubular stub is preferably larger than an external diameter of the core wire in the area of the tubular stub.

24. The guide wire as claimed in claim 20, characterized in that a diameter of the core wire decreases from a proximal end toward a distal end, preferably such that a flexibility of the guide wire increases continuously from the proximal end of the core wire toward the guide-wire tip.

25. The guide wire as claimed in claim 20, characterized in that the wire coil consists of a single wire, in that the area of the wire coil is free of an additional membrane, and in that exactly three different tubular parts are provided with substantially the same external diameter.

\* \* \* \* \*